(12) United States Patent
Brunel

(10) Patent No.: US 6,585,702 B1
(45) Date of Patent: Jul. 1, 2003

(54) SINGLE-USE DEVICE FOR INJECTION

(75) Inventor: Marc Brunel, Toulouse (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/499,644

(22) Filed: Feb. 8, 2000

(30) Foreign Application Priority Data

Oct. 7, 1999 (FR) ............................................. 99 12501

(51) Int. Cl.$^7$ ............................. A61M 5/32; A61M 5/00
(52) U.S. Cl. ...................................... 604/263; 604/198
(58) Field of Search ................................ 604/192–199, 604/232, 234, 263, 110, 162, 164.08, 134, 135, 198, 111

(56) References Cited

U.S. PATENT DOCUMENTS

| 5,137,516 A | 8/1992 | Rand et al. |
| 5,147,325 A | 9/1992 | Mitchell et al. |
| 5,624,402 A | * 4/1997 | Imbert ........................ 604/111 |
| 5,697,908 A | * 12/1997 | Imbert et al. ................ 604/110 |
| 5,709,662 A | * 1/1998 | Olive et al. ................. 604/135 |

FOREIGN PATENT DOCUMENTS

| FR | 2 770 405 | 5/1999 |
| WO | WO 93/02728 | 2/1993 |

* cited by examiner

Primary Examiner—Brian L. Casler
Assistant Examiner—Matthew DeSanto
(74) Attorney, Agent, or Firm—Young & Thompson

(57) ABSTRACT

A single-use device for injection includes a pre-filled syringe with a front nose which supports an injection needle which is protected by a protective cap, and a syringe body which accommodates the syringe. The device further includes a joining piece with claws which can be extended radially to cover and grasp the protective cap by penetrating the cap. The syringe body includes a front section, which can be separated, that is delimited by a breakable area. The front section includes a neck that clamps the tabs of the joining piece onto the protective cap.

12 Claims, 10 Drawing Sheets

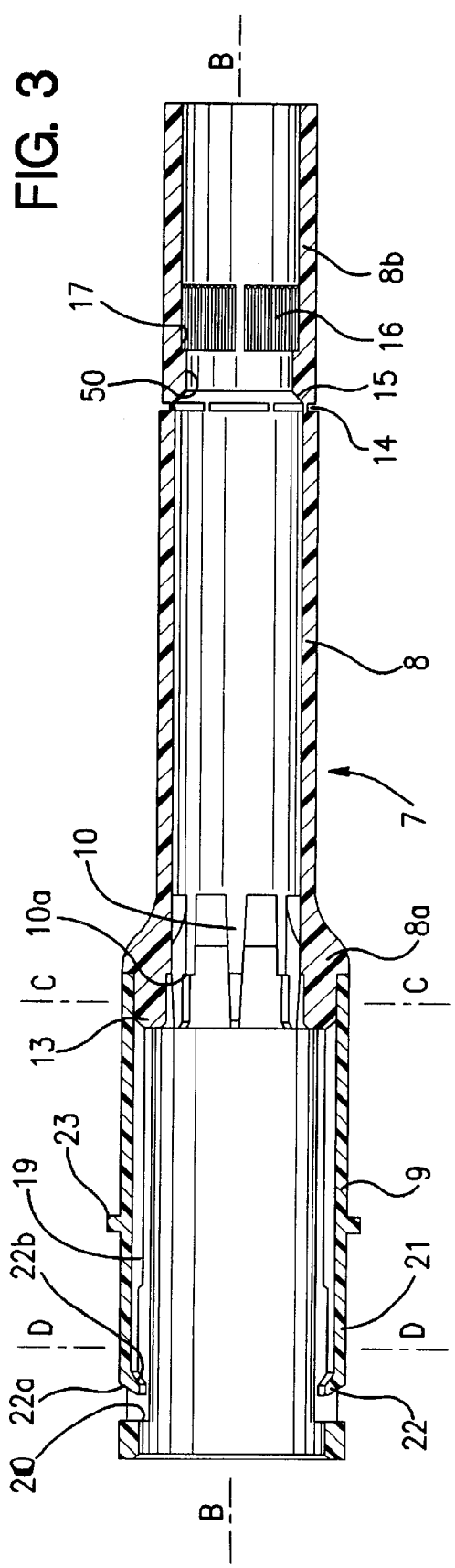
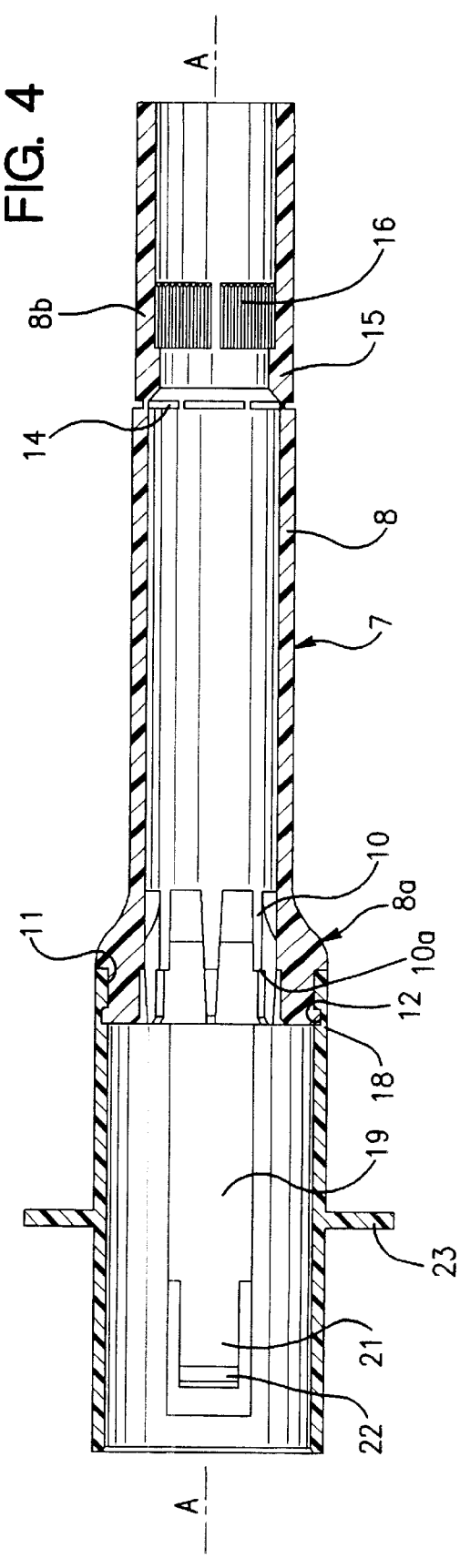

1

SINGLE-USE DEVICE FOR INJECTION

BACKGROUND OF THE INVENTION

The invention relates to a single-use device for injection, comprising a pre-filled syringe which is provided with a front nose, and supports an injection needle which is protected by a protective cap, and a syringe body which accommodates the said syringe, and is provided with means for locking of the latter in rotation and in translation.

At present, for safety reasons, some injection devices of the above-described type comprise a protective joining piece for the cap, which also serves the purpose of facilitating removal of the protective cap.

These protective joining pieces, which are generally designed to be fitted on the front end of the syringe body, additionally comprise a central sleeve, which is designed to cover the protective cap, and is provided with grasping claws which are clipped onto the rear of the said cap.

Although in practice, protective joining pieces of this type make it possible to fulfil the required objectives, they have a major disadvantage, which consists of the fact that the central sleeve is fitted onto the protective cap by being forced, and, when this fitting takes place, it tends to push this cap rearwards during passage of the sealing neck with which the front nose of conventional syringes is conventionally provided.

The fact of thrusting the cap rearwards in this manner can have two detrimental consequences. In fact, firstly, it can cause damage to the end of the needle, which conventionally is stuck into the cap. In addition, it can give rise to breakage of the seal between the protective cap and the nose of the syringe, at the sealing neck of the latter.

SUMMARY OF THE INVENTION

The object of the present invention is to eliminate these disadvantages, and its main objective is to provide a device for injection which is provided with a safety system for protection of the protective cap, which permits easy removal of the latter, and is not likely to damage the needle or detract from the sealing.

For this purpose, the invention relates to a device for injection as described in the foregoing preamble, characterised in that:

- it comprises a joining piece, known as a joining piece with claws, which consists of a front wall, and at least two tabs which can be extended radially, and extend longitudinally relative to the front wall, which can cover the protective cap, and are provided with at least one inner claw for grasping the said cap;
- the syringe body has an open rear front surface which can permit introduction of the syringe, and an opposite front section, which can be separated, and is delimited by a breakable area, which is disposed such as to be positioned substantially at the front nose of the syringe which is accommodated in the said syringe body, the said section which can be separated comprising a neck which is designed to clamp the tabs of the joining piece with claws, such that the latter ensure that the protective cap is grasped;
- the said section which can be separated and the joining piece with claws being provided with conjugated means for locking in translation and in rotation of the latter relative to one another.

According to the invention, and firstly, the joining piece with claws is simply positioned on the protective cap, before the syringe is introduced into the syringe body, and is actually clamped onto the said cap by radial deformation of the tabs at the neck, with which the section which can be separated is provided.

This solution, which consists of trapping the protective cap by means of radial deformation of the tabs of the joining piece with claws, leads to elimination of the risks of damaging the needle and breaking the seal.

However, in order to guarantee this absence of risks, and preferably, each grasping claw of the joining piece with claws is positioned such as to ensure that the protective cap is grasped substantially downstream from the sealing neck.

In addition, according to the invention, the section which can be separated constitutes a protective element which has undeniable advantages in terms of safety, and of inviolability of the protection. In addition, as a result of the locking in rotation and in translation relative to one another of this section which can be separated and of the joining piece with claws, breakage of the breakable area makes it possible to remove simultaneously the said section which can be separated and the joining piece with claws, together with the protective cap which is trapped in the latter, thus providing release directly of the injection needle.

It should also be noted that since the breakage of the breakable area is obtained conventionally by imparting movement of rotation to the section which can be separated, the protective cap is also rotated during this breakage, and its detachment is thus greatly facilitated.

According to an advantageous embodiment, the means for relative locking in rotation and translation of the joining piece with claws and the section which can be separated comprise:

- a plurality of longitudinal catches, which are provided on at least one of the tabs of the joining piece with claws, such as to be positioned downstream from the neck of the section which can be separated of the syringe body, when the syringe is accommodated in the latter; and
- a plurality of longitudinal catches which are provided in the section which can be separated, downstream from the neck of the latter, such that the said neck forms a shoulder for stoppage in translation of the joining piece with claws.

In addition, advantageously, the longitudinal catches which are provided in the section which can be separated, are distributed around the entire periphery of the inner surface of the said section which can be separated, such as to dispense with the need to mark the relative angular positioning of the joining piece with claws and of the section which can be separated.

In addition, in order to facilitate by-passing of the neck, and advantageously, the longitudinal catches of each tab of the joining piece with claws are disposed on a boss, which is provided with an inclined front portion, forming a ramp which is designed to facilitate passage of the neck.

For the same purpose, and advantageously, the neck of the section which can be separated consists of an inner boss, provided with an inclined rear portion which forms an access ramp.

Additionally, in order to ensure that the protective cap is trapped satisfactorily, the neck is advantageously disposed such that it is positioned at the grasping claws of the joining piece with claws.

According to an advantageous embodiment, the joining piece with claws comprises four longitudinal tabs which are distributed regularly relative to the axis of the front wall, two of the said diametrically opposite tabs comprising a boss, and the two others, which are known as the grasping tabs, comprising at least one grasping claw.

In addition, advantageously, the grasping tabs each comprise two lateral grasping claws.

BRIEF DESCRIPTION OF THE DRAWINGS

Other characteristics, objects and advantages of the invention will become apparent from the following detailed description provided with reference to the attached drawings, which show by way of example a preferred, non-limiting embodiment. In these drawings:

FIG. 3 is a longitudinal cross-section through an axial plane A of this protective sheath;

FIG. 4 is a longitudinal cross-section through an axial plane B of this protective sheath;

DESCRIPTION OF THE PREFERRED EMBODIMENTS

Figure 1:
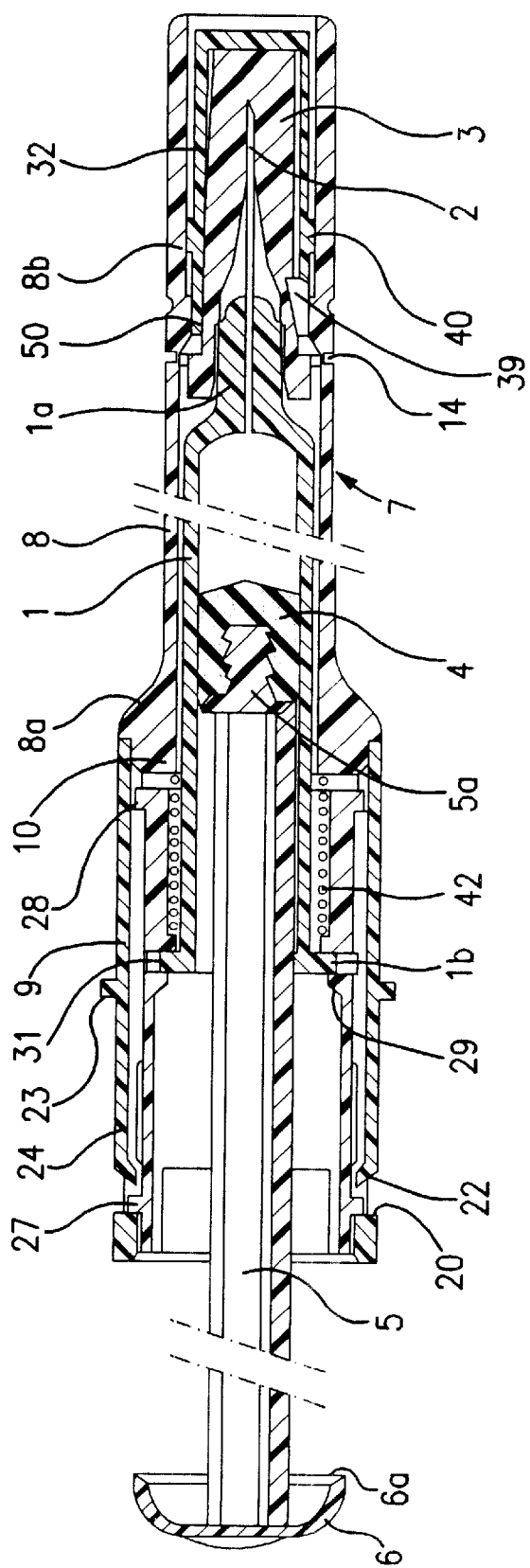
FIG. 1 is a longitudinal cross-section through an axial plane, of a device according to the invention for injection, shown before it is used.
Figure 2:
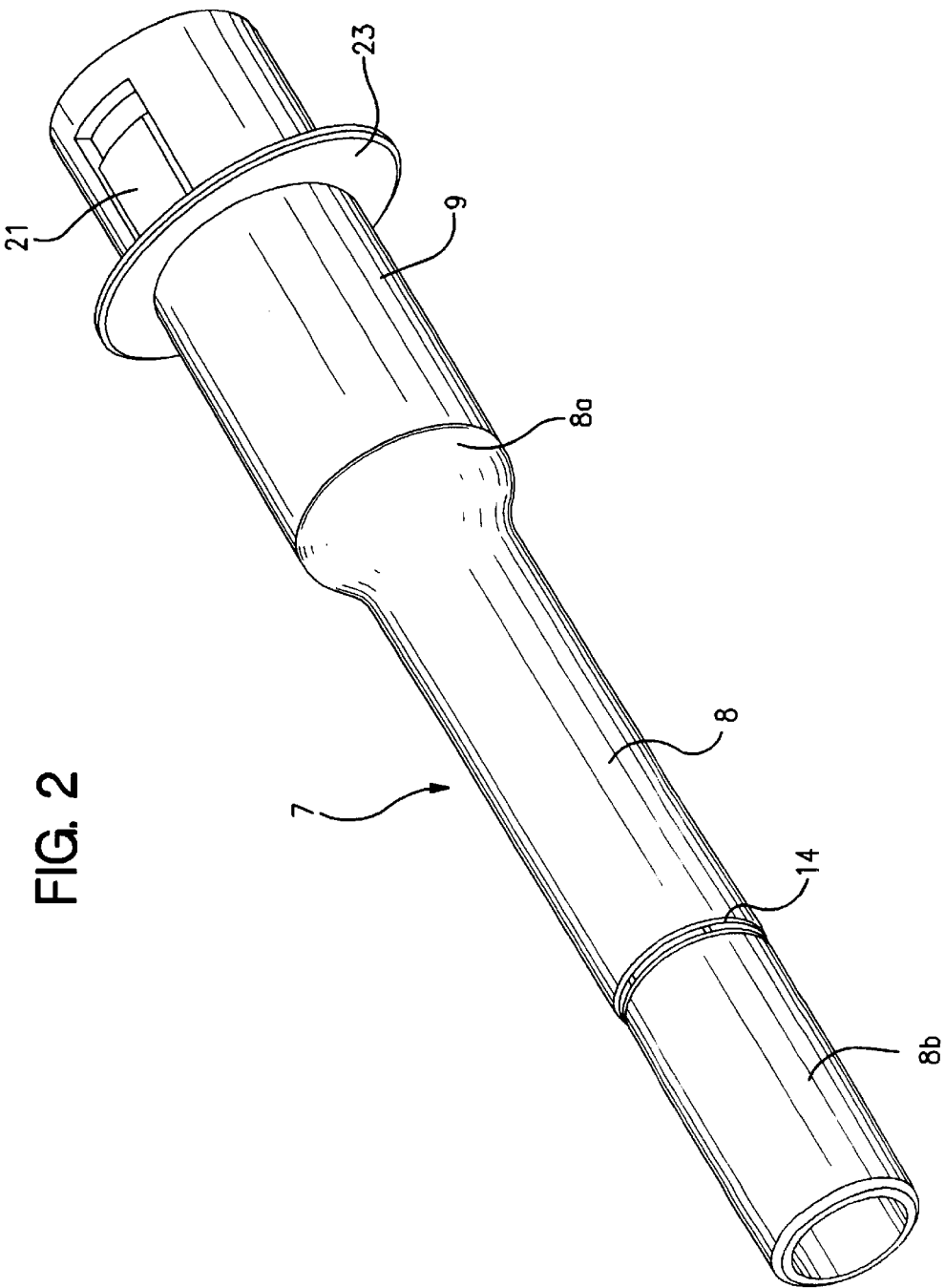
FIG. 2 is a perspective view of the protective sheath of this device for injection.

The device according to the invention for injection shown in FIG. 1 comprises firstly a pre-filled syringe 1 of the conventional type, which for example is made of glass, comprising in a conventional manner a front nose 1a, onto which there is fitted a needle 2, and a collar 1b at its rear end.

This syringe 1 also comprises in a conventional manner a cap 3 for protection of the needle 2, which is designed to be fitted in a sealed manner on the front nose 1a of the said syringe.

It also comprises in a conventional manner a piston 4, which delimits the chamber filled with a dose of fluid, which contains a blind threaded bore, into which there is screwed the threaded end 5a of a piston rod 5, which is provided at its opposite end with a thruster 6.

According to the invention, this thruster 6 is in the form of a bowl, which has a section 6a with an oblique profile, for the purposes explained hereinafter.

The injection device according to the invention also comprises an assembly for protection of the syringe 1, which is designed to be fully pre-assembled before the said syringe, which is initially pre-filled, is put into place in the said protective assembly.

This protective assembly comprises firstly a protective sheath 7, which is shown in FIGS. 2 to 6, consisting of two, front 8 and rear 9 tubular bodies, which are designed to be fitted one in the extension of the other.

The front body 8 has an inner diameter which is conjugated relative to the outer diameter of the syringe 1, and a length which is designed to accommodate the needle 2 provided with its protective cap 3, and is substantially 80% of the length of the syringe 1.

At its rear end, this front body 8 comprises a rear section 8a which has a substantially ovoidal outer shape, with outer diameters which are larger than the regular outer diameter of the said front body, and is hollow on the interior, such as to comprise inner longitudinal ribs such as 10, which define an inner diameter identical to that of the regular inner diameter of this front body 8.

Each of these ribs 10 additionally has a shoulder 10a, which delimits a rear end portion with an inner diameter which is substantially larger than the diameter of the syringe 1.

Figure 5:
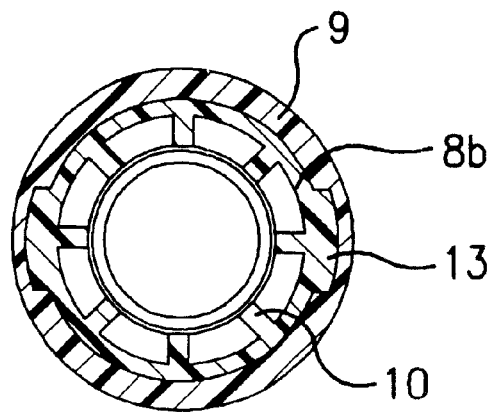
FIG. 5 is a transverse cross-section through a plane C of this protective sheath.
Figure 6:
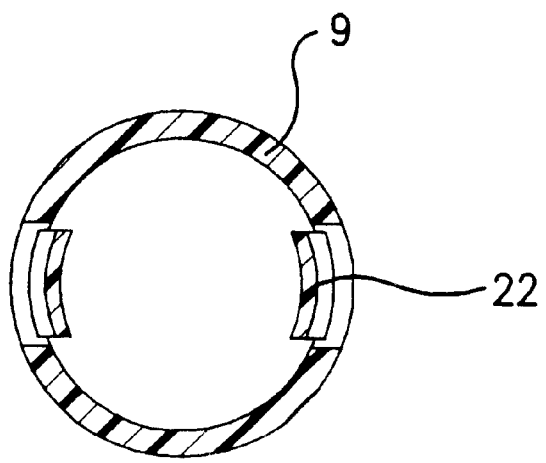
FIG. 6 is a transverse cross-section through a plane D of this protective sheath.

On the outer side, this rear section 8a comprises an annular groove 11 which is delimited by a rear clip ring 12. In addition, as shown in FIG. 5, this groove 11 is interrupted by two lugs such as 13, which are diametrically opposite, and project radially relative to the clip ring 12.

At its front end, the front body 8 comprises a front section 8b which can be separated, and is delimited by a breakable annular area 14, which is positioned such as to be disposed substantially at the front nose 1a of the syringe 1, when the latter has been put into place.

This section 8b which can be separated has on its interior, at its rear end, an oblique profile 15, which forms a ramp, delimiting a rear portion which constitutes a neck 50, with a diameter which is substantially smaller than that of the regular inner diameter of the front body 8.

At the front of this rear portion, the section 8b which can be separated additionally comprises a plurality of longitudinal catches such as 16, distributed on the periphery of the inner surface of the said section which can be separated, and delimiting an inner diameter which is identical to that of the said rear portion, such that the bases of the said catches define a shoulder 17 together with the front end of this rear portion.

Finally, with reference to this section 8b which can be separated, the front portion of the latter which is disposed at the front of the catches 16 has an inner diameter which is identical to the diameter which separates the base of the catches.

The rear body 9 has a substantially ovoidal shape, which is conjugated relative to that of the rear section 8a of the front body 8, and is designed to be fitted onto the said rear section 8a.

For this purpose, this rear body 9 firstly comprises an inner annular groove 18, which is designed to accommodate the clip ring 12. It also comprises two inner, diametrically opposite longitudinal grooves such as 19, which can each accommodate a lug 13, such as to ensure locking in rotation of the two bodies 8, 9, the said grooves being interrupted at a short distance from the rear end of this rear body 9, such that the latter has an inner shoulder 20 at the level of the end of these grooves 19.

Figure 7:
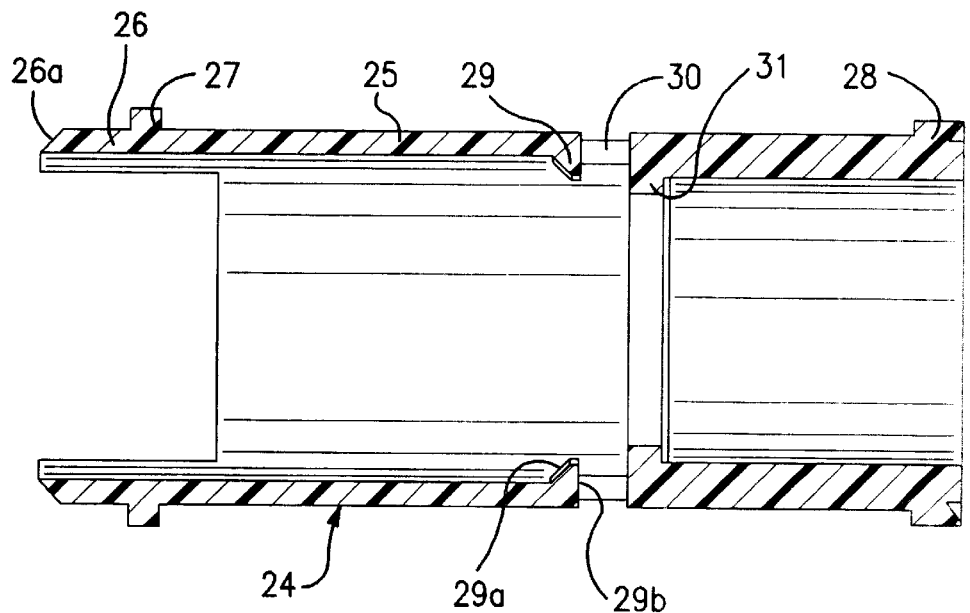
FIG. 7 is a longitudinal cross-section through an axial plane E of the locking ring of this device for injection.
Figure 8:
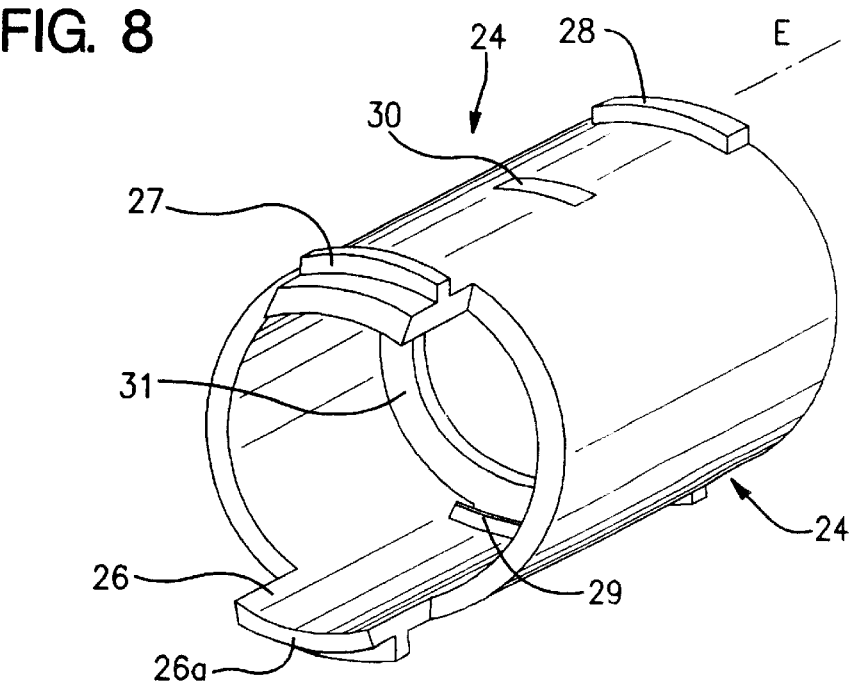
FIG. 8 is a perspective view of this locking ring.

As shown in FIG. 7, the grooves 19 are provided according to the larger diameter of the rear body 9, such as to minimise the thickness of the wall of the said rear body.

The rear body 9 additionally has two deformable tabs such as 21, each of which is provided in a groove 19 at the rear end of the latter, and each of which is formed from a cut-out in the shape of a U provided in the wall of the said rear body.

At its rear end, each of these tabs 21 comprises a transverse hook 22, which projects inside the rear body 9. Each of these hooks comprises a substantially radial anti-return rear surface 22a, and an oblique front surface 22b which forms a ramp.

Finally, the rear body 9 comprises a conventional finger-support outer collar 23.

Secondly, the protective assembly comprises a locking ring 24, which has a shape which is designed to be inserted in the rear body 9, when it is presented opposite the front surface of the latter.

This locking ring 24, which has a length which is designed to be inserted in the rear body 9, is in the form of a cylindrical sleeve 25, which is prolonged at the rear by two tabs such as 26, which are diametrically opposite one another in the form of a sector of a cylinder.

Each of these two tabs 26 has firstly a rear end surface 26a with an oblique profile, which is complementary relative to that of the section 6a of the thruster 6 of the piston rod 5.

Also, substantially half-way along its length, each of these tabs 26 comprises a transverse outer rib 27, which is designed to be able to slide in one of the grooves 10 of the rear body 9.

Centred on the same generatrices as the transverse ribs 27, the cylindrical sleeve 25 of this locking ring 24 comprises two transverse ribs such as 28, which are also designed to slide in the grooves 10 of the rear body 9, and are provided at the front end of the said sleeve.

Substantially half-way along its length, and axially aligned with the aforementioned ribs 27, 28, this cylindrical sleeve 25 also comprises two diametrically opposite inner ribs such as 29, downstream from each of which the peripheral wall of the said sleeve is provided with an aperture such as 30, which permits ejection of the undercut piece.

Each of these inner ribs 29 has a rear surface 29a with an oblique profile which forms a ramp, and an anti-return locking radial front surface 29b.

Finally, downstream from the apertures 30, and at a distance from the inner ribs 29 which is conjugated relative to the thickness of the collar 1b of the syringe 1, the cylindrical sleeve 25 comprises an annular inner shoulder 31.

Figure 9:
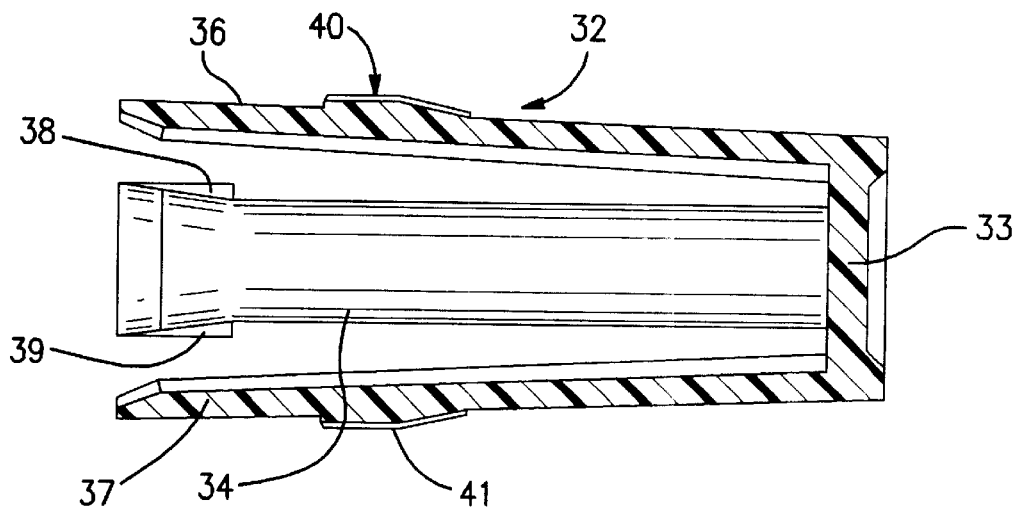
FIG. 9 is a longitudinal cross-section through an axial plane F of the claw-type joining piece of this device for injection.
Figure 10:
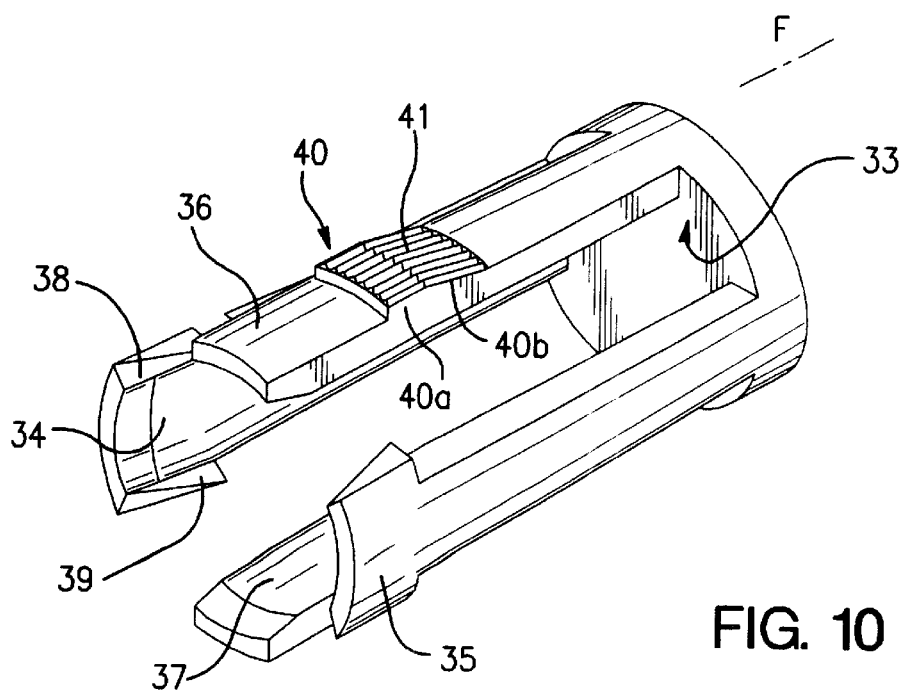
FIG. 10 is a perspective view of this claw-type joining piece.

Finally, the injection device according to the invention comprises a joining piece 32 with claws, which is shown in FIGS. 9 and 10, and is designed to cover the protective cap 3, and to give rise to withdrawal of the latter after breakage of the breakable area 14 of the front body 8 of the protective sheath 7.

This joining piece 32 with claws has a cylindrical front wall 33, with a diameter which is designed to penetrate in the section 8b which can be separated, at the periphery of which there extend substantially at right-angles four separate longitudinal tabs 34, 35, 36, 37, which are distributed regularly relative to the axis of the said wall:

two tabs 34, 35 which are diametrically opposite, and are each provided at their free end with two lateral claws such as 38, 39, which are designed to be able to penetrate in the protective cap 3; and two other diametrically opposite tabs 36, 37, each of which has in an intermediate position along its length an outer boss such as 40, with an outer surface provided with longitudinal catches such as 41, which are conjugated relative to the catches 16 of the section 8b which can be separated. In addition, each boss 40 has a cylindrical rear portion 40a, which is preceded by an inclined front portion 40b which forms a ramp.

It should also be noted that, as shown in FIG. 9, when bedding-in takes place, the tabs 34–37 are in a substantially "open" position, i.e. they are inclined towards the exterior relative to the axis of the front wall 33.

Production of the above-described device for injection, as well as the interconnection of the various units of the component elements, is explained hereinafter with reference to FIGS. 11a to 11f.

Figure 11A:
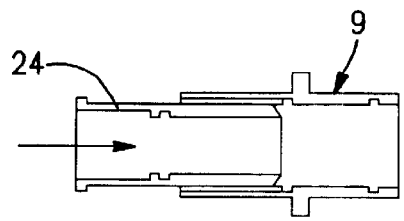
FIGS. 11a to 11f are schematic views showing the successive production steps of this device for injection.

The first step consists of introducing the locking ring 24 into the rear body 9 of the protective sheath 7, by presenting the latter opposite the front surface of the said rear body, until the ribs 27 abut the shoulder 20 (FIG. 11a). It should be noted that this putting into place is permitted by the resilience of the tabs 21, and the shape of the front surface 22b of the ribs 22, which forms a ramp which allows the said ribs to be by-passed.

It should also be noted that when the locking ring 24 has been put into position, it is locked in rotation relative to the rear body 9, as a result of the positioning of the ribs 27 in the grooves 19.

Figure 11B:
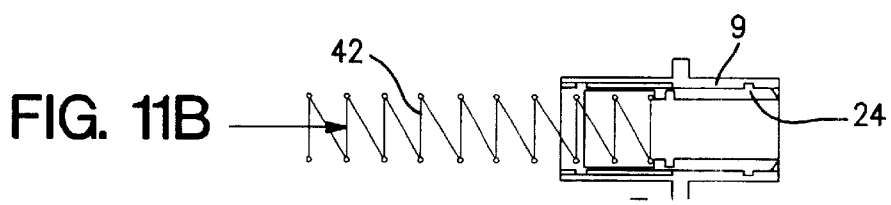

The second step consists of introducing a spiral spring 42 partially inside the locking ring 24, by presenting the latter opposite the front surface of the said ring, until one of its ends abuts the shoulder 31 (FIG. 11b).

Figure 11C:
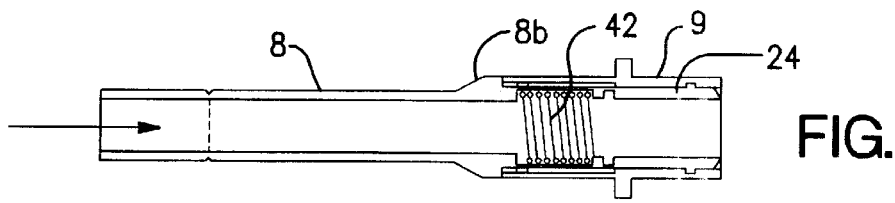

The third step consists of fitting the front body 8 onto the rear body, by co-operation of the clip ring 12 with the groove 18 (FIG. 11c). During this operation, the spring 42 is automatically compressed between the shoulders 10a of the ribs 10 and the shoulder 31. In addition, the front body 8 and the rear body are locked in rotation relative to one another, as a result of positioning of the lugs 13 in the grooves 19.

On completion of these three operations which can easily be automated, a fully-assembled protective assembly is obtained, inside which there can then be introduced the pre-filled syringe 1, as previously described.

Figure 11D:
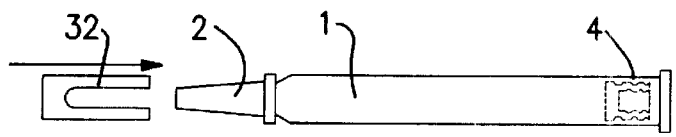

Prior to this introduction, as shown in FIG. 11d, the joining piece 32 with claws is positioned on the protective cap 3 of the syringe 1, which at this stage is without the piston rod 5. During this positioning, the tabs 34–37 of the joining piece 32 with claws are simply positioned around the protective cap 3, without any risk of pushing the latter in, and damaging the needle 2 and/or destroying the seal.

Figure 11E:
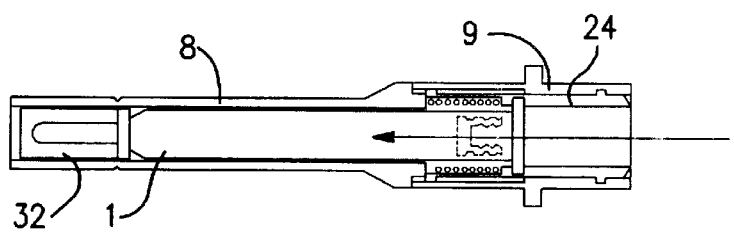

The syringe 1 which is provided with the joining piece 32 with claws is then introduced into the rear body 9 of the protective sheath 7, until the collar 1b is locked between the ribs 29 and the shoulder 31 (FIG. 11e). It should be noted that this introduction is made possible by the fact that the ribs 29 can be deformed, and owing to the ramp-type form of the rear surface 29a of these ribs 29, which allows the latter to be by-passed by the collar 1b.

In addition, during this introduction, the joining piece 32 with claws is clamped on the protective cap 3, when the bosses 40 of the latter pass the level of the ramp 15 of the section 8b which can be separated and the neck 50, which passage is also facilitated by the ramp-type form of the front portion 40b of the said bosses.

It should also be noted that, as shown in FIG. 1, during this clamping, the claws 38, 39 penetrate the protective cap 3 downstream from the glass cone which is conventionally provided on the front nose of conventional syringes 1, and is designed to guarantee sealing. Thus, any risk of pushing in the protective cap 3 and therefore damaging the needle 2 and/or destroying the seal is eliminated.

When this step has been carried out, it should be noted that the joining piece 32 with claws and the protective sheath 7 are locked in rotation relative to one another, as a result of the co-operation of the respective catches 16, 41 of the latter. In addition, firstly, the protective cap 3 is locked in rotation relative to the joining piece 32 with claws, owing to the penetration in the latter of the claws 38, 39, and secondly, this joining piece 32 with claws, the protective sheath 7 and the locking ring 24, are also locked in rotation relative to one another, as previously explained.

Figure 11F:
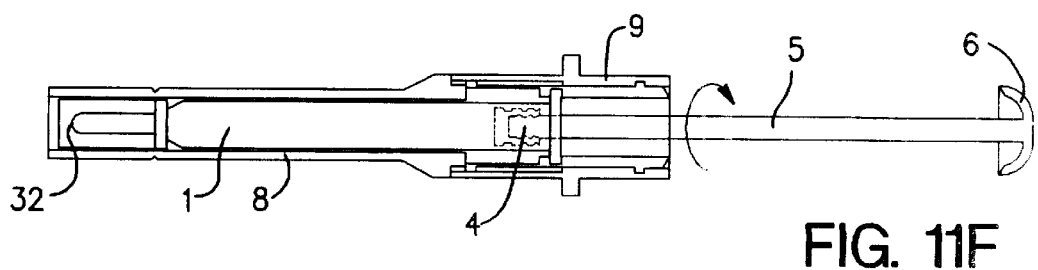

The final step shown in FIG. 11f consists of rendering the piston rod 5 integral with the piston 4 in a conventional manner. This then provides an injection device which is ready to use, use of which is described hereinafter with reference to FIGS. 12 to 14.

Figure 12:
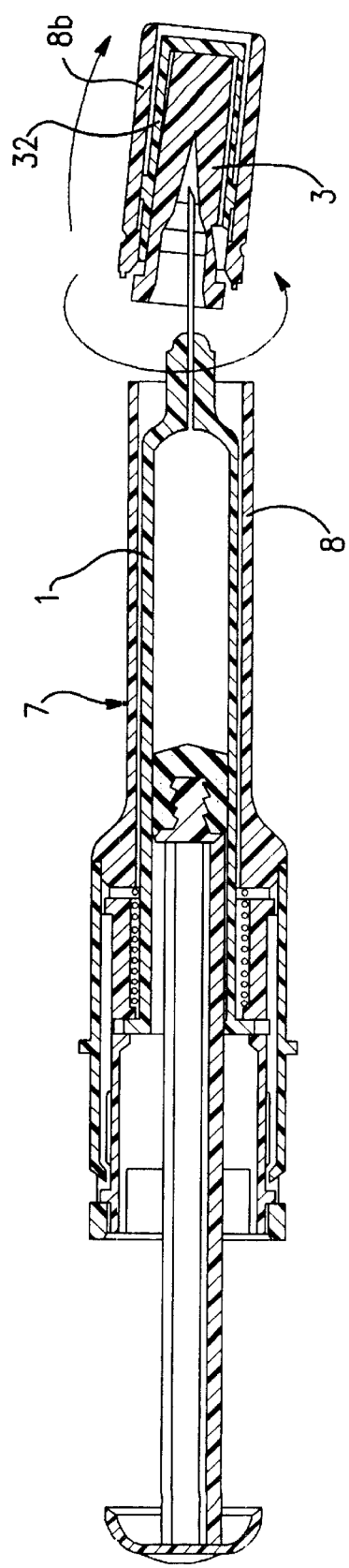
FIG. 12 is a longitudinal cross-section through an axial plane of this device for injection, showing the initial step of removal of the protective cap, for the purpose of use of the said device for injection.

Firstly, as shown in FIG. 12, the initial step consists of breaking the breakable area 14 in a conventional manner, by subjecting the section 8 which can be separated to rotary movement, and pulling this section. During the movement, since the assembled elements (protective cap 3, protective sheath 7, locking ring 24) are locked in rotation relative to one another, the protective cap 3 is firstly made to turn, thus facilitating detachment of the latter, then the joining piece 32 with claws is locked in translation relative to the section 8b which can be separated, by thrusting the bosses 40 against the shoulder 17, such that the protective cap 3 is removed simultaneously with the joining piece 32 with claws and with the said section which can be separated.

Figure 13:
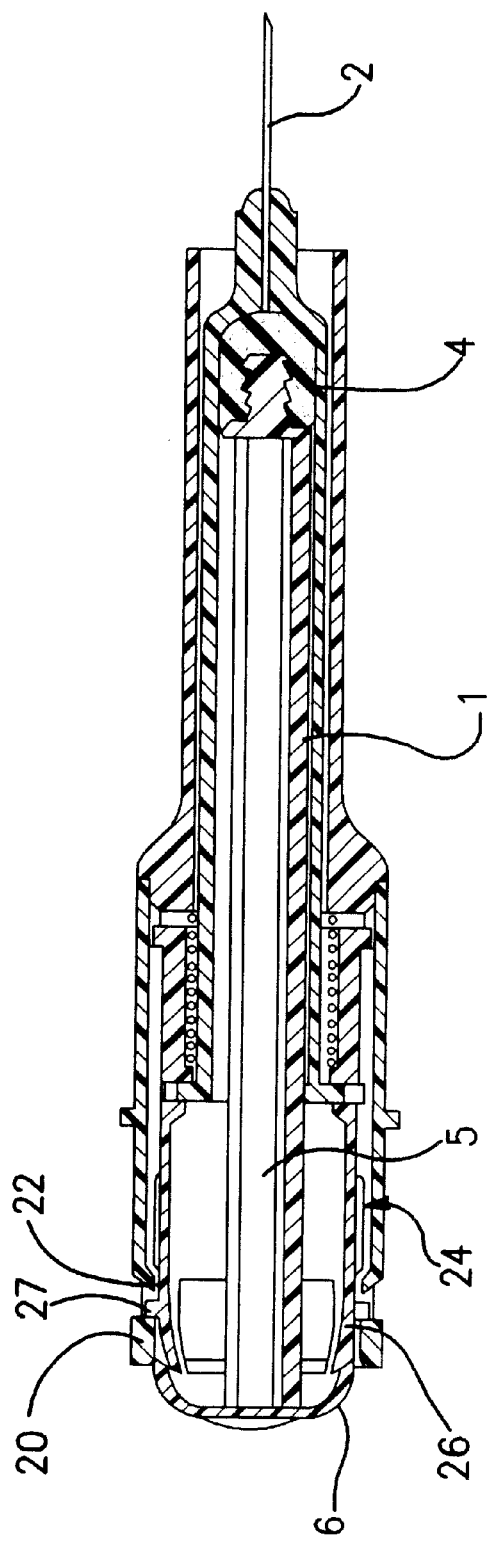
FIG. 13 is a longitudinal cross-section through an axial plane, representing the device for injection on completion of injection.

The injection can then be carried out in a conventional manner by means of antagonistic action on the thruster 6 and the finger-support collar 23. On completion of the injection, as shown in FIG. 13, the profiled edge 6a of the thruster 6 co-operates with the profiled edge 26a of the tabs 26 of the locking ring 24, causing the said tabs 26 to be deformed radially towards the interior, until the ribs 27 are released.

It should also be noted that since the ribs 27 are disposed in an intermediate position on the tabs 26, the latter have a ramp to the rear of the said ribs, which makes it possible to absorb the production tolerances of the syringes 1, and to ensure that the entire dose of fluid is delivered.

Figure 14:
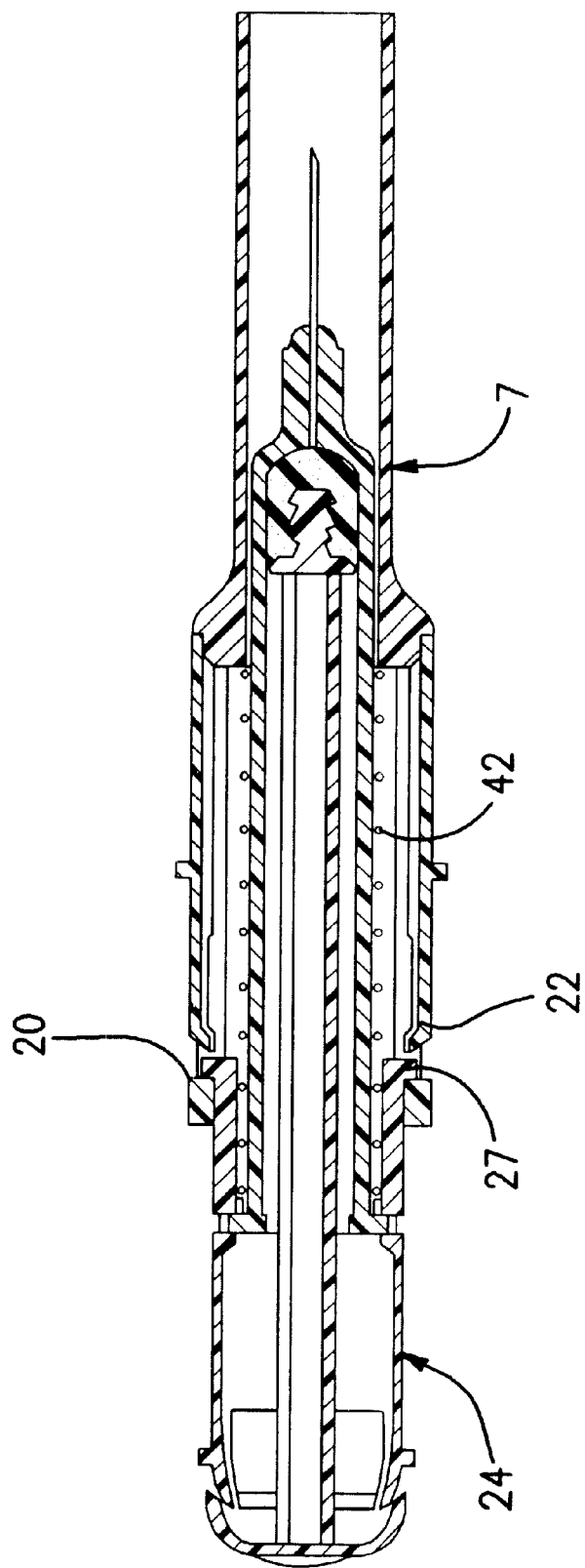
FIG. 14 is a longitudinal cross-section through an axial plane representing the device for injection in the position for protection after it has been used.

As shown in FIG. 14, when the injection has been completed, and force on the thruster 6 has ceased, the locking ring 24, which is thrust by the spring 42, is pushed back inside the protective sheath 7, and entrains the syringe 1, until the ribs 28 by-pass the ramp 22b of the ribs 22, and are locked between the said ribs 22 and the shoulder 20, thus preventing further use of the injection device.

Finally, and advantageously, the front body 8 of the protective sheath 7 is made of a translucent material, so that the syringe 1 can be seen. On the other hand, the rear body 9 of this protective sheath is made of an opaque material, so as to conceal the release mechanism from the sight of the user and the patient.

The locking ring 24 is made of a material which has a colour different from that of the rear body 9, such as to make it possible to identify immediately injection devices which have already been used.

What is claimed is:

1. An injection device comprising:
   a syringe having a needle covered with a protective cap;
   a body housing said syringe, said body having a rear section and a removable front section and a frangible portion that separates said front section from said rear section; and
   a joining piece inside said front section, said joining piece having longitudinally extended tabs that flex radially and cover sides of said protective cap, said tabs having at least one claw that penetrates into said protective cap, said front section having an inner wall that urges said at least one claw into said protective cap.

2. The injection device of claim 1, wherein said joining piece and said front section have interlocking portions that prevent rotation of said joining piece relative to said front section.

3. The injection device of claim 2, wherein said interlocking portion of said joining piece has a ramped surface to facilitate insertion of said joining piece inside said front section during manufacture of the injection device.

4. The injection device of claim 2, wherein said joining piece and said front section portions have abutting lateral surfaces that prevent longitudinal movement of said joining piece relative to said front section.

5. The injection device of claim 1, comprising four of said tabs, two of said tabs having said at least one claw.

6. The injection device of claim 5, wherein two of said tabs comprise bosses that cooperate with said inner wall to prevent rotation of said prevent rotation of said joining piece relative to said front section.

7. The injection device of claim 5, wherein said two of said tabs have two of said at least one claw.

8. The injection device of claim 1, wherein said syringe comprises a sealing neck that attaches said needle to a nose of said syringe, and wherein said at least one claw penetrates into said protective cap beyond said sealing neck.

9. An injection device comprising:
   a syringe having a needle covered with a protective cap having a generally cylindrical outer surface and an end face;
   a body housing said syringe, said body having a rear section and a removable front section and a frangible portion that separates said front section from said rear section;
   a generally cylindrical joining piece inside said front section, said joining piece having an end wall abutting said end face of said protective cap and plural longitudinally extending tabs that flex radially, said tabs being shorter than said protective cap so that distal ends of said tabs are on said generally cylindrical outer surface of said protective cap, said tabs having at least one claw adjacent to one of said distal ends that penetrates into said generally cylindrical outer surface of said protective cap,
   said front section having an inner wall with a diameter relative to said protective cap so that said inner wall pushes and holds said at least one claw into said generally cylindrical outer surface; and
   said tabs having bosses that engage corresponding elevations on said inner wall of said front section that prevent rotation of said joining piece relative to said front section,
   wherein rotation of said front section and removal thereof at said frangible portion simultaneously carries away said joining piece and said protective cover.

10. The injection device of claim 9, wherein said joining piece and said front section portions have abutting lateral surfaces that prevent longitudinal movement of said joining piece relative to said front section.

11. The injection device of claim 9, wherein said syringe comprises a sealing neck that attaches said needle to a nose of said syringe, and wherein said at least one claw penetrates into said generally cylindrical outer surface beyond said sealing neck.

12. The injection device of claim 9, comprising four of said tabs, two of said tabs having said at least one claw.

* * * * *